United States Patent
Koch et al.

(10) Patent No.: US 8,746,245 B2
(45) Date of Patent: Jun. 10, 2014

(54) RESPIRATOR WITH A CIRCUIT FOR BREATHING GAS

(75) Inventors: Jochim Koch, Ratzeburg (DE); Jörg Polzien, Ratzeburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1283 days.

(21) Appl. No.: 12/573,317

(22) Filed: Oct. 5, 2009

(65) Prior Publication Data

US 2010/0108063 A1 May 6, 2010

(30) Foreign Application Priority Data

Nov. 3, 2008 (DE) .................. 10 2008 055 700

(51) Int. Cl.
- *A62B 7/00* (2006.01)
- *A62B 7/10* (2006.01)
- *A62B 19/00* (2006.01)
- *A62B 23/02* (2006.01)
- *A61M 16/00* (2006.01)
- *F24F 5/00* (2006.01)
- *B01D 53/02* (2006.01)
- *F28D 5/00* (2006.01)

(52) U.S. Cl.
USPC ................... 128/204.15; 128/205.12; 95/139; 62/304

(58) Field of Classification Search
USPC .................... 128/204.15–204.16, 204.18, 128/205.12–205.13, 205.15, 200.24, 128/203.12; 95/91, 139; 96/108; 165/225; 62/259.4, 304

See application file for complete search history.

(56) References Cited

U.S. PATENT DOCUMENTS

| | | | |
|---|---|---|---|
| 4,300,547 A | 11/1981 | Pasternack | |
| 4,314,566 A | 2/1982 | Kiwak | |
| 4,635,629 A | 1/1987 | Thorp et al. | |
| 5,269,293 A * | 12/1993 | Loser et al. | 128/204.15 |
| 6,543,247 B2 * | 4/2003 | Strauss | 62/259.3 |
| 6,990,979 B2 | 1/2006 | Koch | |
| 7,802,322 B2 * | 9/2010 | Koch et al. | 2/456 |
| 2002/0144683 A1 | 10/2002 | Gurnee et al. | |
| 2003/0033829 A1 * | 2/2003 | Smith et al. | 62/480 |
| 2005/0197684 A1 * | 9/2005 | Koch | 607/104 |

FOREIGN PATENT DOCUMENTS

| | | |
|---|---|---|
| DE | 879 651 B | 6/1953 |
| DE | 879 851 | 6/1953 |
| DE | 10304394 | 5/2005 |
| GB | 751 099 A | 6/1956 |
| GB | 1194944 A | 6/1970 |
| GB | 2118047 A | 10/1983 |
| GB | 2122907 A | 1/1984 |
| JP | 60137805 A | 7/1985 |

* cited by examiner

*Primary Examiner* — Jackie T Ho
*Assistant Examiner* — Mark K Han
(74) *Attorney, Agent, or Firm* — McGlew and Tuttle, P.C.

(57) ABSTRACT

A gas mask and breathing equipment is provided with a circuit for breathing gas and with a heat exchanger (7) cooled by an evaporating agent. The evaporating agent is introduced from an evaporating agent container (8) into the heat exchanger (7) via at least one group of spraying elements (9) and a gas delivery means (11) allows a gas volume flow to flow through the heat exchanger (7).

20 Claims, 2 Drawing Sheets

RESPIRATOR WITH A CIRCUIT FOR BREATHING GAS

CROSS REFERENCE TO RELATED APPLICATIONS

This application claims the benefit of priority under 35 U.S.C. §119 of German Patent Application DE 10 2008 055 700.5 filed Nov. 3, 2008, the entire contents of which are incorporated herein by reference.

FIELD OF THE INVENTION

The present invention pertains to a device for cooling the breathing gas temperature in a respirator with a circuit for breathing gas and to a process for controlling the cooling of the respirator.

BACKGROUND OF THE INVENTION

In respirators, especially in gas masks and breathing equipment, respiration takes place in a closed circuit to reduce the weight and to increase the use time, and only the amount of oxygen consumed is replaced from a pressurized gas reservoir and fed into the circuit. Enrichment of the carbon dioxide ($CO_2$) breathed out in the circuit to physiologically harmful levels in the circuit must be avoided. An absorber with an absorbent, which extracts the $CO_2$ from the breathing circuit, is present for this in the circuit. Prior-art absorbents consist of one or more alkali hydroxides and contain or consist especially of calcium hydroxide. The absorbents are contained in respirators in a breathing lime absorber, a so-called alkali cartridge used as a replaceable part. Heat and moisture are generated during the chemical reaction taking place between the $CO_2$ and the absorbent. The heat leads to a rise in the breathing gas temperature and may thus lead to a physical compromise for the person respirated by means of the respirator. Temperatures 25° C. above the ambient temperature were measured in experimental measurements in the breathing gas saturated with moisture at the outlet of the breathing lime absorber.

One solution to eliminate this problem is to condition the breathing air in closed-circuit gas masks and breathing equipment, which are used for a use time of several hours, i.e., to both cool the breathing air and reduce the quantity of moisture in the circuit.

The cooling of the breathing lime absorber with the use of paraffin or the use of a salt as a coolant for such respirators is disclosed in DE 879 851 B, where the evaporation or melt temperature is between 40° C. and 180° C. and the breathing lime absorber is surrounded by the coolant. The breathing lime absorber is used as a heat exchanger rather than the breathing gas being cooled directly. The use of a separate heat exchanger, in which the exchange of the amount of heat is brought about by the motion of the air generated by the breathing bag, is known from U.S. Pat. No. 4,635,629. The exchanged amount of heat is thus not adapted to the breathing gas temperature and cannot be influenced by a control circuit. Cooling of the breathing lime absorber with an evaporating agent by means of the external evaporative cooling via the housing of the lime absorber is known from DE 10304394 B4 (U.S. Pat. No. 6,990,979). The use of a fan is known from the same document DE 10304394 B4 to increase the amount of air and to improve as a consequence the heat exchange.

SUMMARY OF THE INVENTION

The object of the present invention is to provide a respirator with a circuit for breathing gas with a regulated and improved conditioning for the breathing gas and to provide a process for regulating the respirator.

According to the invention, a gas mask and breathing equipment is provided comprising a circuit for breathing gas as well as a heat exchanger connected to the circuit, the heat exchanger being cooled by an evaporating agent and including a first duct for the breathing gas and a second duct, the first duct of the heat exchanger being thermally and mechanically coupled with the second duct of the heat exchanger via a heat exchange surface. An evaporating agent container is provided with evaporating agent. A spraying element is provided for introducing the evaporating agent from the evaporating agent container into the second duct of the heat exchanger via the spraying element. A gas delivery means is provided to send a gas volume flow through the second duct of the heat exchanger, the first duct being located on an incoming flow side of a user of the gas mask and breathing equipment.

According to another aspect of the invention, a process is provided for regulating a gas mask and breathing equipment. The process comprises the steps of providing a circuit for breathing gas and connecting a heat exchanger to the circuit. The heat exchanger is cooled by an evaporating agent and includes a first duct for the breathing gas and a second duct. The first duct of the heat exchanger is thermally and mechanically coupled with the second duct of the heat exchanger via a heat exchange surface. The process further includes providing an evaporating agent container with evaporating agent, providing a spraying element, introducing the evaporating agent from the evaporating agent container into the second duct of the heat exchanger via the spraying element and providing a gas delivery means. The gas delivery means sends a gas volume flow through the second duct of the heat exchanger with, the first duct being located on an incoming flow side of a user of the gas mask and breathing equipment.

The process further may include the steps of providing a temperature sensor, providing a pressure sensor, providing a control unit, detecting and analyzing signals of the temperature sensor and of the pressure sensor by the control unit and controlling the conditioning of the breathing gas. The control unit switches on the gas delivery means, for sending a gas volume flow, by means of an actuating signal based on breathing gas temperature exceeding a first temperature limit. The control unit controls an adjusting valve in terms of the duration of the opening time, for introducing the evaporating agent, by means of an actuating signal based on breathing gas temperature exceeding a second temperature limit of the breathing gas temperature.

The first temperature limit of the breathing gas temperature may be preset in the range of 28° C. to 34° C. and the second temperature limit of the breathing gas temperature may be preset in the range of 31° C. to 37° C. The first temperature limit of the breathing gas temperature and the second temperature limit of the breathing gas temperature can be set as a function of the ambient temperature of the site of use. The first temperature limit of the breathing gas temperature and the second temperature limit of the breathing gas temperature can be set as a function of the humidity of the air at the site of use.

An essential advantage of the present invention is the direct cooling of the breathing air in the breathing air duct of an air/air heat exchanger. As a result, cooling is more efficient than cooling via the outer surface of a lime absorber. The ergonomic requirements imposed on the closed-circuit gas mask and breathing equipment do not make it possible to use freely selectable geometric embodiments of the outer surface of the breathing lime absorber for the external cooling, so that an optimal thermal coupling of the largest possible number of breathing lime pellets in a narrow space with the outer surface of the breathing lime absorber is possible only conditionally. By contrast, nearly the entire amount of breathing gas circulating in a circuit can be cooled with a separate air/air heat exchanger. The air/air heat exchanger comprises a first inner duct for the breathing gas circuit and a second outer duct for the cooling gas circuit. The air in the cooling circuit is cooled down by means of the evaporative cooling by ambient air being caused to flow through the second duct by means of a gas delivery means and by a liquid evaporating agent being introduced into the second duct of the heat exchanger. The evaporating agent in the second duct is preferably introduced directly to the heat exchange surface between the first and second ducts.

A material possessing good thermal conductivity, for example, a metal, is preferably used as the material for the heat exchange surface.

The liquid evaporating agent is applied in the second duct directly onto the heat exchange surface by spray nozzles arranged in the second duct and is distributed there. As a result, the heat exchange surface is cooled directly, on the one hand, by the direct contact with the liquid evaporating agent, and, on the other hand, the air in the second duct of the air/air heat exchanger is cooled at a heat exchange surface due to the evaporation of the particles of evaporating agent.

An electrically driven positive displacement blower designed as a fan, which delivers a gas volume flow of preferably 150 L to 250 L per minute uniformly along the second duct of the heat exchanger in order to achieve evaporation of the evaporating agent, especially water, an aqueous solution or a mixture with water, which cools the air in the second duct, is used as a gas delivery means to deliver the air in the second duct in the simplest case. The amount of heat generated in the breathing lime absorber and contained in the breathing gas is removed in this manner to the outside as a result.

A gas volume flow of at least 150 L per minute has proved to be necessary to generate the amounts of convection air, which are different for the heat transport in the second duct. Both a parallel-flow heat exchanger and a counterflow heat exchanger may be used as the heat exchanger, the selection of the corresponding type being dependent on the dimensions in space of the closed-circuit gas mask and breathing equipment and the arrangement of the components gas delivery means, high-pressure oxygen cylinder, lime absorber, breathing bag and evaporating agent container in the closed-circuit gas mask and breathing equipment, which arrangement is dictated by the dimensions.

The evaporating agent, preferably water, can be provided in an evaporating agent container. The pressure of the oxygen cylinder, 200 bar, is brought to a working pressure of 5 bar by means of a pressure reducer. The pressure is then reduced further by means of a dispensing nozzle, so that oxygen is introduced into the breathing circuit at a rate ranging from 1 L/minute to 2 L/minute.

For a use time of 4 hours and with the user of the respirator having a respiratory minute volume of 30 L per minute, the amount of thermal energy generated in about 3 L of breathing lime is about 750 kJ. Conditioning improved according to the present invention can be achieved, while the limitations dictated by the weight and size of the closed-circuit gas mask and breathing equipment are taken into account at the same time, with the removal of a thermal energy of 450 kJ.

The quantity of water needed as an evaporating agent to cool the thermal energy of 450 kJ is 0.25 L, which is provided in the evaporating agent container for injection into the second duct of the heat exchanger under a pressure of 2 bar to 6 bar. The heat exchanger is designed for cooling the thermal energy of 450 kJ to a thermal output of 30 W. A pressure in the range of 2 bar to 6 bar is set via a reducing nozzle at the outlet of the evaporating agent container for operating the spraying elements. The spraying elements spray the evaporating agent by means of an adjusting valve onto the heat exchange surface of the heat exchanger. A control unit sends a control signal to the adjusting valve. The adjusting valve is opened and closed cyclically in a cycled manner.

To measure the breathing gas temperature, a temperature sensor is arranged in the breathing gas circuit in the first duct of the heat exchanger at the breathing gas outlet to the user of the gas mask and breathing equipment and is electrically connected to the control unit.

To spray the evaporating agent into the second duct, a pressure must be admitted to the evaporating agent. In a preferred embodiment, this pressure can be made available by the oxygen cylinder present in the closed-circuit gas mask and breathing equipment.

In an optional embodiment, the evaporating agent may be maintained under a pressure already in the evaporating agent container itself, in which case the evaporating agent container is introduced into the gas mask and breathing equipment as a consumable agent for the operation, for example, in the form of a cartridge. The necessary pressure in the range of 2 bar to 6 bar is admitted now to the evaporating agent by a propellant gas reservoir arranged in the evaporating agent container.

In another preferred embodiment, the evaporating agent container is a consumable part, in which case the evaporating agent container is designed as a cartridge that is under pressure.

In another embodiment according to the present invention, the spraying elements are arranged in the duct of the air/air heat exchanger at different angles in relation to the heat exchange surface of the heat exchanger in order to achieve distribution of the evaporating liquid over the entire area on the heat exchange surface. The preferred angle range of the array of spraying elements is in an angle range of 30° to 90° in relation to the heat exchange surface.

The cooling of the breathing gas by means of the gas volume flow in the second duct of the heat exchanger, the quantity of evaporating agent sprayed in via the group of spraying elements, and the operating pressure set on the evaporating agent container are regulated in the following manner: the gas delivery means is activated above a predetermined first breathing gas temperature of 30° C., the spraying elements are activated when a second, predetermined breathing gas temperature of 35° C. is exceeded, and they spray quantities of evaporating agent into the second duct in a cycled manner. The first and second breathing gas temperatures are preset by a presetting means within the temperature limits of 28° C. to 34° C. for the first breathing gas temperature and within the temperature limits of 31° C. to 37° C. for the second. In a special embodiment of the process according to the present invention, the temperature limits are adapted to the needs in the use of the gas mask and breathing equipment. The ambient temperature and humidity of the air at the site of use are parameters that make changes in the predefined first and second breathing gas temperatures necessary.

An exemplary embodiment of the present invention will be explained below on the basis of the schematic figure.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
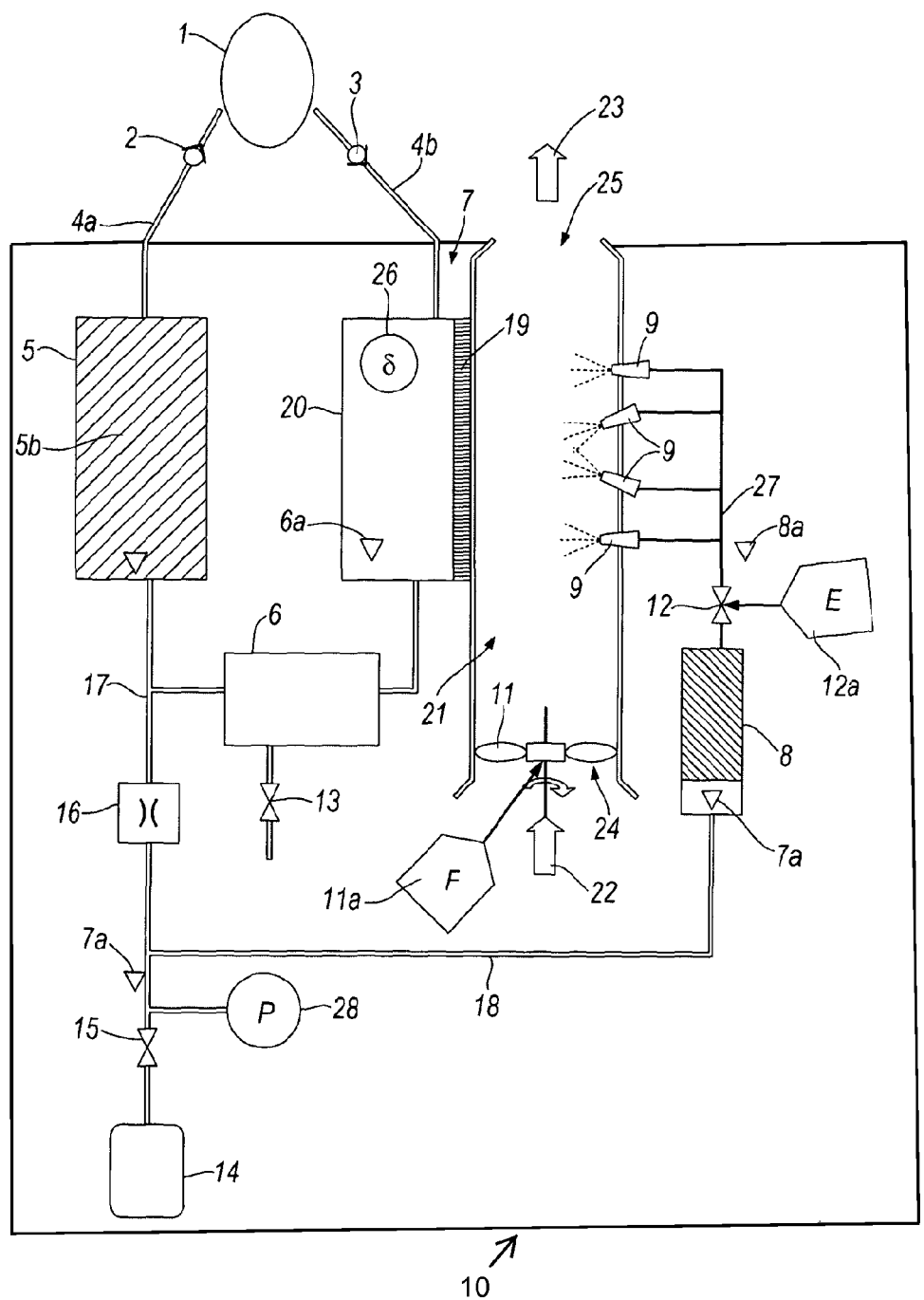
FIG. 1 is a schematic diagram of a closed-circuit gas mask and breathing equipment according to the invention with the components necessary for cooling the breathing air.

Referring to the drawings in particular, FIG. 1 shows a respirator housing 10, in which a breathing lime absorber 5, an air/air heat exchanger 7, an evaporating agent container 8, nonreturn valves 2, 3, a breathing bag 6, a group of spraying elements 9, a fan 11, an adjusting valve 12, a drain valve 13, a high-pressure oxygen cylinder 14, a pressure reducer 15, a dispensing nozzle 16, delivery lines 17, 18, and a temperature sensor 26 are arranged.

The expired air of the respirator user is released via the expiration breathing tube 4a and the nonreturn valve 2 to the breathing lime absorber 5. The user of the gas mask and breathing equipment again inspires via an inspiration breathing tube 4b and the nonreturn valve 3. The user inspires through the first duct 20 of the air/air heat exchanger from the breathing bag 6, which is connected to the breathing lime absorber 5. The circuit for the breathing gas is thus closed.

The gas from the high-pressure oxygen cylinder 14 is reduced to a working pressure 7a of 5 bar in the closed-circuit gas mask and breathing equipment 10 with a pressure reducer 15 and reduced to the breathing pressure 6a via a first pressure line 17 and a dispensing nozzle 16 and fed into the circuit, and the oxygen consumed is replaced. The working pressure 7a of 5 bar is admitted to the evaporating agent container 8 from the outlet of the pressure reducer 15 via a second pressure line 18. The evaporating agent is fed under the operating pressure 8a to the group of spraying elements 9 via an adjusting valve 12 and the feed line 27. The spraying elements 9 are arranged such that they are directed towards the heat exchange surface 19 in the second duct 21 in the air/air heat exchanger 7 and can spray the full area of the heat exchange surface 19 with evaporating agent. The arrangement of the individual spraying elements 9 may be selected to be at right angles to the heat exchange surface 19, but it is also advantageous for achieving wetting of the heat exchange surface 19 over a large area to direct the spraying elements at an angle differently from one another in an angle range of 30° to 90° in relation to the heat exchange surface 19. The size of the evaporating agent container 8 is selected to be such that it stores a sufficient amount of evaporating agent for the duration of use by the user of the respirator or the respirator. In case of water, 250 mL to 450 mL are sufficient for a use time of four hours.

The ambient air is drawn in the direction of the first arrow 22 of the air inlet opening 24 and is discharged on the opposite side in the direction of the second arrow 23 through an outlet opening 25. The air now sweeps over the second duct 21 of the air/air heat exchanger 7 and removes the evaporated evaporating agent, especially water, with the air being delivered into the environment. The group of spraying elements 9 comprises at least one spraying element. In the arrangement shown in FIG. 1, four spraying elements 9 are shown as an example, but a smaller or greater number of spraying elements 9 is also covered by the solution according to the present invention. The spraying elements 9 are activated in a control circuit with inclusion of the breathing gas temperature. The breathing gas temperature is detected via a temperature sensor 26 at the outlet of the first duct 20 of the air/air heat exchanger 7.

A drain valve 13, via which the liquid collected in the circuit can be drawn off into the environment, is arranged at the breathing bag 6.

Figure 2:
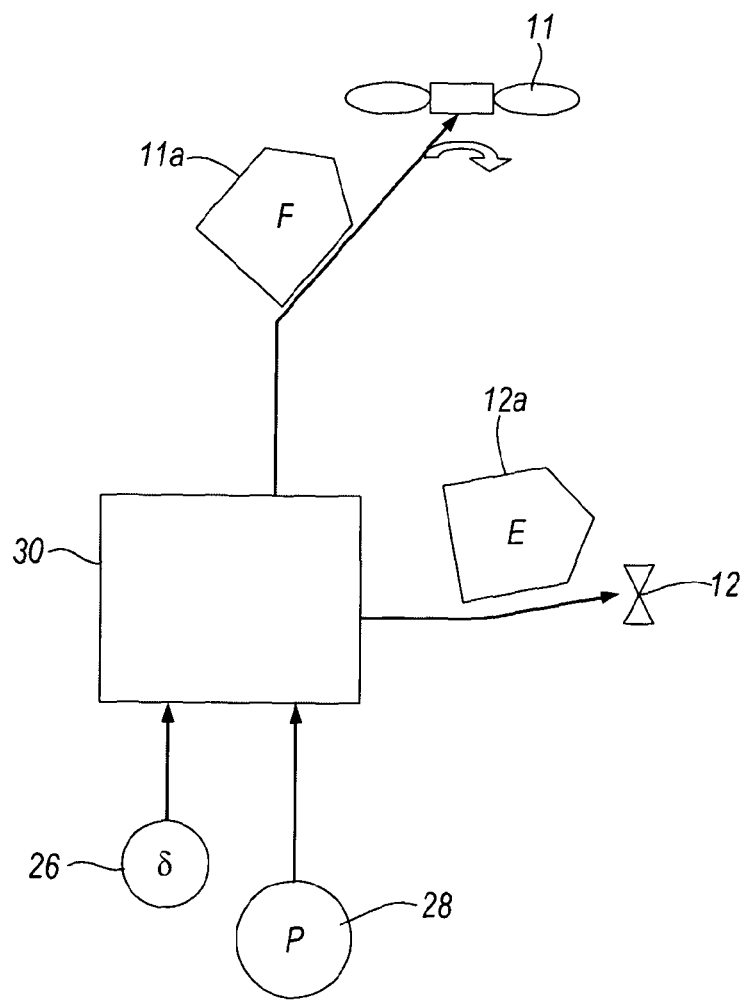
FIG. 2 is a schematic view of the arrangement of the components necessary for regulating the cooling of a closed-circuit gas mask and breathing equipment.

FIG. 2 shows a control unit 30, to which the temperature sensor 26 and the pressure sensor 28 are connected.

The control unit 30 is designed to control the amount of air of the fan 11 by means of an actuating signal F indicated by reference symbol 11a. The amount of air can be adjusted in the simplest manner by varying the speed of fan 11. Furthermore, the control unit 30 is designed to open and close the adjusting valve 12 by means of an actuating signal E indicated by reference symbol 12a. The quantity of evaporating agent flowing through the adjusting valve 12 in a cycled manner is obtained from the particular opening angles of the spraying elements 9 and the operating pressure 8a of the evaporating agent present at the adjusting valve 12. The control unit 30 is designed for this to derive the opening cycle time for the adjusting valve 12 from the signal and to correspondingly actuate the adjusting valve 12 by means of the actuating signal E. The control unit 30 is designed, furthermore, to determine the working pressure 7a from the signal of the pressure sensor 28 and to include it in the setting of the opening cycle time for the adjusting valve 12.

While specific embodiments of the invention have been described in detail to illustrate the application of the principles of the invention, it will be understood that the invention may be embodied otherwise without departing from such principles.

Appendix

LIST OF REFERENCE NUMBERS

1 User of gas mask and breathing equipment
2 First nonreturn valve
3 Second nonreturn valve
4a Expiration breathing tube
4b Inspiration breathing tube
5 Breathing lime absorber
5b Breathing lime pellets
6 Breathing bag
6a Breathing pressure
7 Air/air heat exchanger
7a Working pressure
8 Evaporating agent container
8a Operating pressure
9 Group of spraying elements
10 Respirator housing
11 Gas delivery means, fan
11a Actuating signal E for the fan
13 Adjusting valve
12a Actuating signal F for the adjusting valve
13 Drain valve
14 High-pressure oxygen cylinder
15 Pressure reducer
16 Dispensing nozzle
17 First delivery line
18 Second delivery line
19 Heat exchange surface
20 First duct in the air/air heat exchanger
21 Second duct in the air/air heat exchanger 22 Direction of first arrow of air flow
23 Direction of second arrow of air flow
24 Air inlet opening
25 Air outlet opening
26 Temperature sensor
27 Feed line
28 Pressure sensor
30 Control unit

What is claimed is:

1. A gas mask and breathing equipment comprising:
a circuit for breathing gas;
a heat exchanger connected to said circuit, said heat exchanger being cooled by an evaporating agent and said heat exchanger including a first duct for the breathing gas and a second duct, said first duct of said heat exchanger being thermally and mechanically coupled with the second duct of the heat exchanger via a heat exchange surface;
an evaporating agent container with evaporating agent;
a spraying element configured to directly apply said evaporating agent across a surface defining at least a portion of said second duct;
a gas delivery means to send a gas volume flow through said second duct of said heat exchanger, said first duct being located on an incoming flow side of a user of the gas mask and breathing equipment.

2. A gas mask and breathing equipment in accordance with claim 1, further comprising:
a carbon dioxide absorber, said heat exchanger being located at a spaced location from said carbon dioxide absorber, wherein the evaporating agent is introduced into said second duct via said spraying element through an adjusting valve positioned between said evaporating agent container and said spraying element.

3. A gas mask and breathing equipment in accordance with claim 2, wherein an operating pressure is admitted to the evaporating agent container, the gas delivery means being a positive displacement blower driven electrically or by means of a pressurized gas.

4. A gas mask and breathing equipment in accordance with claim 3, wherein the operating pressure is admitted to the evaporating agent container by the pressure of a pressurized gas cylinder via a second pressurized gas line.

5. A gas mask and breathing equipment in accordance with claim 3, wherein the evaporating agent container is provided with a propellant gas reservoir, which propellant gas reservoir is placed under the operating pressure.

6. A gas mask and breathing equipment in accordance with claim 2, wherein the evaporating agent is water, a solution containing water or a mixture containing water.

7. A gas mask and breathing equipment in accordance with claim 2, wherein the spraying element is directed in an angle range of 30° to 90° in relation to the heat exchange surface of the heat exchanger.

8. A process for regulating a gas mask and breathing equipment, the process comprising:
providing a circuit for breathing gas;
connecting a heat exchanger to the circuit, the heat exchanger being cooled by an evaporating agent and said heat exchanger including a first duct for the breathing gas and a second duct, the first duct of the heat exchanger being thermally and mechanically coupled with the second duct of the heat exchanger via a heat exchange surface of said heat exchanger;
providing an evaporating agent container with the evaporating agent;
providing a spraying element configured to directly apply said evaporating agent across a surface defining at least a portion of said second duct;
introducing the evaporating agent from the evaporating agent container into the second duct of the heat exchanger via the spraying element;
providing a gas delivery means; and
sending a gas volume flow through the second duct of the heat exchanger with the gas delivery means, the first duct being located on an incoming flow side of a user of the gas mask and breathing equipment.

9. A process in accordance with claim 8, further comprising the steps of:
providing a temperature sensor;
providing a pressure sensor;
providing a control unit;
detecting and analyzing signals of the temperature sensor and of the pressure sensor by the control unit;
controlling a conditioning of the breathing gas, wherein the control unit switches on the gas delivery means, for said sending said gas volume flow, by means of an actuating signal based on a breathing gas temperature exceeding a first temperature limit and the control unit controls an adjusting valve in terms of a duration of an opening time, for said introducing the evaporating agent, by means of an actuating signal based on the breathing gas temperature exceeding a second temperature limit of the breathing gas temperature, said adjusting valve being located between said evaporating agent container and said spraying element.

10. A process in accordance with claim 9, wherein the first temperature limit of the breathing gas temperature is preset in a range of 28° C. to 34° C. and the second temperature limit of the breathing gas temperature is preset in a range of 31° C. to 37° C.

11. A process in accordance with claim 9, wherein the first temperature limit of the breathing gas temperature and the second temperature limit of the breathing gas temperature can be set as a function of an ambient temperature of a site of use.

12. A process in accordance with claim 9, wherein the first temperature limit of the breathing gas temperature and the second temperature limit of the breathing gas temperature can be set as a function of the humidity of the air at a site of use.

13. A process in accordance with claim 9, wherein the gas delivery means is a positive displacement blower driven electrically or by means of a pressurized gas.

14. A process in accordance with claim 9, wherein an operating pressure is admitted to the evaporating agent container.

15. A process in accordance with claim 14, wherein the operating pressure is admitted to the evaporating agent container by the pressure of a pressurized gas cylinder via a second pressurized gas line.

16. A process in accordance with claim 14, wherein the evaporating agent container is provided with a propellant gas reservoir, which propellant gas reservoir is placed under the operating pressure.

17. A process in accordance with claim 9, wherein the evaporating agent is water, a solution containing water or a mixture containing water.

18. A process in accordance with claim 9, wherein the spraying element is directed in an angle range of 30° to 90° in relation to the heat exchange surface of the heat exchanger.

19. A process in accordance with claim 8, further comprising the steps of:

providing a carbon dioxide absorber, said heat exchanger being located at a spaced location from said carbon dioxide absorber, said carbon dioxide absorber being connected to said circuit;

delivering expired breathing fluid to said carbon dioxide absorber.

20. A gas mask and breathing equipment comprising:

a circuit for breathing gas;

a carbon dioxide absorber connected to said circuit, said carbon dioxide having an inlet for receiving expired breathing gas and an outlet;

a heat exchanger connected to said circuit, said heat exchanger comprising a first duct, a second duct and a heat exchange surface, said heat exchanger being cooled by an evaporating agent, said first duct having a first duct inlet receiving the breathing gas and a first duct outlet, said first duct being thermally and mechanically coupled with the second duct of the heat exchanger via said heat exchange surface;

an evaporating agent container with said evaporating agent;

a spraying element configured to directly apply said evaporating agent across a surface defining at least a portion of said second duct;

a gas delivery means to send a gas volume flow through said second duct of said heat exchanger, said first duct being located on an incoming flow side of a user of the gas mask and breathing equipment.

* * * * *